US011793981B2

(12) United States Patent
McAninch (10) Patent No.: US 11,793,981 B2
(45) Date of Patent: Oct. 24, 2023

(54) MICRONEEDLE DEVICE FOR CONTROL OF THYROID HORMONE LEVELS (71) Applicant: Equilibrate Therapeutics, LLC, Santa Barbara, CA (US)

(72) Inventor: Elizabeth A. McAninch, Chicago, IL (US)

(73) Assignee: EQUILIBRATE THERAPEUTICS, LLC, Santa Barbara, CA (US)

(*) Notice: Subject to any disclaimer, the term of this patent is extended or adjusted under 35 U.S.C. 154(b) by 267 days.

(21) Appl. No.: 17/327,221

(22) Filed: May 21, 2021

(65) Prior Publication Data

US 2021/0361921 A1 Nov. 25, 2021

Related U.S. Application Data (60) Provisional application No. 63/028,268, filed on May 21, 2020.

(51) Int. Cl.
*A61M 3/00* (2006.01)
*A61P 5/14* (2006.01)
(Continued)

(52) U.S. Cl.
CPC ....... *A61M 37/0015* (2013.01); *A61K 31/198* (2013.01); *A61K 45/06* (2013.01);
(Continued)

(58) Field of Classification Search
CPC ...... A61M 37/0015; A61M 2037/0023; A61M 2037/003; A61M 2037/0046;
(Continued)

(56) References Cited

U.S. PATENT DOCUMENTS 6,334,856 B1  1/2002 Allen
6,503,231 B1  1/2003 Prausnitz
(Continued)

FOREIGN PATENT DOCUMENTS

CN  109568567   4/2019
WO  2008051291  5/2008
WO  2018226160  12/2018

OTHER PUBLICATIONS

Abdalla, et al., "Defending plasma T3 is a biological priority", Clin. Endocrinol., 81(5):633-641 (2014).
(Continued)

*Primary Examiner* — Amber R Stiles
(74) *Attorney, Agent, or Firm* — PABST PATENT GROUP LLP (57) ABSTRACT Described is a microneedle device, preferably a controlled release device, for delivery of liothyronine (LT3 or salt thereof) to a patient with hypothyroidism and/or who is not pregnant. The microneedle device contains LT3 or salt thereof in an effective amount to maintain normal, stable levels, in the serum, of free and/or total T3. The microneedle device includes at least two components: multi-dimensional array of microneedle(s) and a substrate to which the base of the microneedle(s) are secured or integrated. The microneedles contain LT3 or salt thereof as well as a biodegradable and/or biodissolvable polymer, such as polyvinyl pyrrolidone for controlled release of LT3 or salt thereof. Also described are methods of making and using the microneedle device.

26 Claims, 5 Drawing Sheets (51) Int. Cl.
| | |
|---|---|
| *A61K 9/00* | (2006.01) |
| *A61M 37/00* | (2006.01) |
| *A61K 31/198* | (2006.01) |
| *A61K 45/06* | (2006.01) |

(52) U.S. Cl.
CPC .............. *A61M 2037/003* (2013.01); *A61M 2037/0023* (2013.01); *A61M 2037/0046* (2013.01); *A61M 2037/0061* (2013.01); *A61M 2202/0078* (2013.01); *A61M 2205/32* (2013.01)

(58) Field of Classification Search
CPC .. A61M 2037/0061; A61M 2202/0078; A61M 2205/32; A61M 2037/0053; A61K 31/198; A61K 45/06; A61K 9/0021; A61K 2300/00; A61P 5/14
See application file for complete search history.

(56) References Cited

U.S. PATENT DOCUMENTS

| | | | |
|---|---|---|---|
| 6,611,707 | B1 | 8/2003 | Prausnitz |
| 7,226,439 | B2 | 6/2007 | Prausnitz |
| 2003/0147943 | A1 | 8/2003 | Luo |
| 2004/0156893 | A1 | 8/2004 | Klein |
| 2008/0154210 | A1 | 6/2008 | Jordan |
| 2015/0182703 | A1* | 7/2015 | Fohrman ............. A61M 5/3295 604/173 |
| 2019/0105261 | A1* | 4/2019 | Waugh ................. A61K 31/167 |
| 2022/0296866 | A1* | 9/2022 | Taylor ....................... A61F 2/04 |

OTHER PUBLICATIONS

Alomari, et al., "Printing T3 and T4 oral drug combinations as a novel strategy for hypothyroidism", Int. J. of Pharm., 549:363-369 (2018).
Bakhteyar, et al., "Kinetic Analysis of Drug Release from Compounded Slow-release Capsules of Liothyronine Sodium (T3)", International Journal of Pharmaceutical Compounding, 21(5):418-425 (2017).
Barth, et al., "Comparison of method-related reference intervals for thyroid hormones: studies from a prospective reference population and a literature review", Annals of Clinical Biochemistry, 55(1):107-112 (2018).
Bauer, et al., "Risk for fracture in women with low serum levels of thyroid-stimulating hormone", Ann. Intern. Med., 134(7):561-568 (2001).
Biondi, et al., "Effects of chronic subclinical hyperthyroidism from levothyroxine on cardiac morphology and function", Cardiologia, 44(5):443-449 (1999). with English Abstract.
Chu, et al., "Fabrication of Dissolving Polymer Microneedles for Controlled Drug Encapsulation and Delivery: Bubble and Pedestal Microneedle Designs", J. of Pharm. Sciences, 99(10):4228-4238 (2010).
Chu, et al., "Separable arrowhead microneedles". J. of Contr. Rel., 149:242-249 (2011).
Conceiçao, et al., "Metal Coordinated Poly-Zinc-Liothyronine Provides Stable Circulating Triiodothyronine Levels in Hypothyroid Rats", Thyroid, 28(11):1425-1433 (2018).
Garber, et al., "Clinical practice guidelines for hypothyroidism in adults: cosponsored by the American Association of Clinical Endocrinologists and the American Thyroid Association", Endocr. Pract., 18(6):988-1028 (2012).
Gullo, et al., "Levothyroxine Monotherapy Cannot Guarantee Euthyroidism in All Athyreotic Patients", PLoS One, 6: e22552 (2011).
Henry, et al., "Micromachined Needles for the Transdermal Delivery of Drugs," Proceedings MEMS 98. IEEE. Eleventh Annual International Workshop on Micro Electro Mechanical Systems. An Investigation of Micro Structures, Sensors, Actuators, Machines and Systems, 494-98 (1998).
Huang, et al., "Type 3 Iodothyronine Deiodinase Is Highly Expressed in the Human Uteroplacental Unit and in Fetal Epithelium", The J. of Clin. Endocrinology & Metabolism, 88(3):1384-1388 (2003).
International Search Report for corresponding PCT application PCT/US2021/033588 dated Sep. 14, 2021.
Jo, et al., "Type 2 deiodinase polymorphism causes ER stress and hypothyroidism in the brain", The J. of Clin. Invest., 1-16 (2018).
Jonklaas, et al., "Guidelines for the Treatment of Hypothyroidism", Thyroid, 24(12):1670-1751 (2014).
Li, et al., "Rapidly separable microneedle patch for the sustained release of a contraceptive", Nat. Biomed. Eng., 3(3):220-229 (2019).
Mcaninch, et al., "The History and Future of Treatment of Hypothyroidism", Ann. Intern. Med., 164(1):50-56 (2016).
Mccanich, et al., "Systemic Thyroid Hormone Status During Levothyroxine Therapy in Hypothyroidism: A Systematic Review and Meta-Analysis", K. Clin. Endocrinol. Metab., 103(12):4533-4542 (2018).
Peterson, et al., Supporting Information, "Is a Normal TSH Synonymous With "Euthyroidism" in Levothyroxine Monotherapy?", J. Clin. Endocrinol. Metab., 101(12):4964-4973 (2016).
Peterson, et al., "Is a Normal TSH Synonymous With "Euthyroidism" in Levothyroxine Monotherapy?", J. Clin. Endocrinol. Metab., 101(12):4964-4973 (2016).
Santini, et al., "Role for Inner Ring Deiodination Preventing Transcutaneous Passage of Thyroxine", The J. of Clin. Endo. & Metab., 88(6):2825-2830 (2003).
Saravanan, et al., "Twenty-four hour hormone profiles of TSH, Free T3 and free T4 in hypothyroid patients on combined T3/T4 therapy", Exp. Clin. Endocrinol. Diabetes, 115(4):261-267 (2014).
Sawin, et al., "Low serum thyrotropin concentrations as a risk factor for atrial fibrillation in older persons", New Engl. J. Med., 331(19):1249-1252 (1994).
Than, et al., "Self-implantable double-layered micro-drug-reservoirs for efficient and controlled ocular drug delivery", Small Methods, 1:1700269 (2017b).
Than, et al., "Transdermal Delivery of Anti-Obesity Compounds to Subcutaneous Adipose Tissue with Polymeric Microneedle Patches", Small Methods, 1:1700269 (2017a).
Than, et al., Suppoprting Information, "Transdermal Delivery of Anti-Obesity Compounds to Subcutaneous Adipose Tissue with Polymeric Microneedle Patches", Small Methods, 1:1700269 (2017c).
Waghule, et al., "Microneedles: A smart approach and increasing potential for transdermal drug delivery system", Biomedicine & Pharmacotherapy, 109:1249-1258 (2019).
Welsh, et al., "How reliable are free thyroid and total T3 hormone assays?", Eur. J. Endocrinol., 175(6):R255-R263 (2016).
Whitehead, et al., "Discovery of synergistic permeation enhancers for oral drug delivery", J. Control. Release, 128(2):128-133 (2008a).
Whitehead, et al., "Safe and effective permeation enhancers for oral drug delivery", Pharm. Res., 25(8):1782-1788 (2008b).

\* cited by examiner

MICRONEEDLE DEVICE FOR CONTROL OF THYROID HORMONE LEVELS

CROSS-REFERENCE TO RELATED APPLICATIONS

This application claims the benefit of and priority to U.S. Application No. 63/028,268, filed on May 21, 2020, which is hereby incorporated herein by reference in its entirety.

FIELD OF THE INVENTION

The invention is in the field of drug delivery devices, particularly microneedle devices for transdermal delivery of thyroid hormones, triiodothyronine (liothyronine) and thyroxine (levothyroxine), to patients having hypothyroidism.

BACKGROUND OF THE INVENTION

Hypothyroidism affects more than 10 million Americans and hundreds of millions of people worldwide (Jonklaas, et al., Thyroid 2014, 24:1670-1751). Thyroid hormone replacement therapy has been used as a treatment strategy for hypothyroidism for over a century (McAninch and Bianco, Ann. Intern. Med. 2016, 164:50-56). For most of the twentieth century, natural thyroid preparations (thyroid extract, desiccated thyroid, or thyroglobulin) containing thyroxine (T4) and triiodothyronine (T3) dominated the market (McAninch and Bianco, Ann. Intern. Med. 2016, 164:50-56).

T4 is the primary secretory pro-hormone of the thyroid gland, which provides a rationale for levothyroxine (LT4), the synthetic form of T4, being the standard of care for thyroid hormone replacement therapy (Jonklaas, et al., Thyroid 2014, 24:1670-1751; McAninch and Bianco, Ann. Intern. Med. 2016, 164:50-56). Outside of the thyroid, one iodine atom is removed from T4, thereby converting it to the active hormone, T3, by enzymes called deiodinases (types I and II). The thyroid gland also secretes T3, but in lesser quantities than it secretes T4. Whether LT4 treatment restores thyroid hormone signaling within all tissues remains controversial. Evidence of persistent signs and symptoms of hypothyroidism during LT4 therapy at doses that normalize serum thyroid stimulating hormone (TSH) is mounting. Studies of hypothyroid patients in the US and Europe revealed that patients receiving LT4 displayed about 10% lower serum levels of T3 (Gullo, et al., PLoS One. 2011; 6:e22552; Peterson, et al., J. Clin. Endocrinol. Metab. 2016, 101(12):4964-4973; Conceiçao, et al., Thyroid 2018, 28(11), 1425-1433; McAninch and Bianco, Ann. Intern. Med. 2016, 164:50-56). Recent evidence suggests that this 10% difference in serum T3 levels can have significant clinical consequences. About 10-20% of LT4-treated patients have residual symptoms of hypothyroidism and report lower well-being despite supposedly adequate LT4 treatment (McAninch and Bianco, Ann. Intern. Med. 2016, 164:50-56; Peterson, et al., J. Clin. Endocrinol. Metab. 2016, 101(12): 4964-4973; Conceiçao, et al., Thyroid 2018, 28(11), 1425-1433). Also, thyroid hormone dependent markers, such as serum cholesterol and basal metabolic rate, can remain abnormal in LT4-treated patients with normal serum TSH levels (McAninch, et al., J. Clin. Endocrinol. Metab. 2018, 103, 4533-4542). This evidence supports the need for new treatment options for hypothyroidism (Jonklaas, et al., Thyroid 2021, 31(2), 156-182).

Alternatively, liothyronine (LT3), the synthetic form of T3 has been used in treatment of hypothyroidism (McAninch and Bianco, Ann. Intern. Med. 2016, 164:50-56; Bakhteyar, et al., International Journal of Pharmaceutical Compounding 2017, 21(5), 418-425). However, oral LT3 has limited clinical applications, because it has a shorter half-life (hours to two days) compared to oral LT4 (about seven days), exhibits rapid clearance, and absorption that gives rise to high fluctuations in serum levels of T3 (Saravanan, et al., Exp. Clin. Endocrinol. Diabetes 2014, 115:261-267; Bakhteyar, et al., International Journal of Pharmaceutical Compounding 2017, 21(5), 418-425; Jonklaas 2015). This is a major problem, because endogenous serum T3 levels are stable and tightly regulated, fluctuating by less than 10% on a daily basis (Abdalla and Bianco, Clin. Endocrinol. 2014, 81:633-641; Conceiçao, et al., Thyroid 2018, 28(11), 1425-1433). Further, patients displaying even minimally elevated thyroid hormone levels have significantly greater risk for cardiovascular events and hip fractures (Biondi, eg al., Cardiologia 1999, 44:443-449; Sawin, eg al., New Engl. J. Med. 1994, 331:1249-1252; Bauer, et al., Ann. Intern. Med. 2001, 134:561-568; Conceiçao, et al., Thyroid 2018, 28(11), 1425-1433).

While circumventing problems such as short half-life of oral LT3, an improved method of delivering LT3 to achieve stable levels of serum free T3 and/or total T3, remains an unmet need in the treatment of hypothyroidism.

Therefore, it is an object of the invention to provide transdermal delivery systems for improved treatment of hypothyroidism.

SUMMARY OF THE INVENTION

A microneedle device for sustained, controlled transdermal delivery of liothyronine (LT3) or a combination of LT3 and levothyroxine (LT4) to a patient with hypothyroidism is described. The microneedle device contains LT3 or an alkali salt thereof, to produce an effective amount of serum T3 to maintain normal, stable levels of serum total T3 and/or free T3; normalize levels of TSH; and/or maintain a normal free T4:free T3 ratio in a patient suffering from hypothyroidism, who is not a pregnant female. Preferably, the microneedle device is a controlled release device.

The microneedle device includes at least two components: at least one, more preferably more, microneedle(s) and a substrate to which the base of the microneedle(s) are secured or integrated. In some forms, the microneedle(s) are biodegradable and contain LT3 or a salt thereof (e.g., an alkali salt thereof). In these forms, the microneedle(s) contain a biodegradable and/or dissolvable polymer, such as polyvinylpyrrolidone. The microneedles are provided as a multi-dimensional array, in contrast to a microneedle device with a single microneedle or single row of microneedles.

In some forms, the microneedle device further contains at least one reservoir that is not a microneedle, which contains LT3 or a salt thereof (e.g., an alkali salt thereof) and is selectably in fluid connection with the base end of the microneedles, either integrally or separably until the moment of use. Preferably, when the microneedle device contains a reservoir that is not a microneedle, at least one microneedle contains at least one hollow pathway disposed at or between the base end and the tip. In these forms, LT3 or salt thereof (e.g., an alkali salt thereof) is formulated such that the formulation has a viscosity suitable for flowing through a microneedle having a gauge size between 26 Gauge and 31 Gauge, inclusive, between 26 Gauge and 32 Gauge, inclusive, between 26 Gauge and 33 Gauge, inclusive, or between 26 Gauge and 34 Gauge, inclusive.

Also described are methods of making and using the microneedle device. The preferred patient population are individuals with hypothyroidism, who are not pregnant.

BRIEF DESCRIPTION OF THE DRAWINGS

In FIG. 6A, the device contains pedestals and bubbles between the microneedles and a substrate. In FIG. 6B, the device contains a joint between the microneedles and a substrate. In FIG. 6C, the device contains a pedestal between the microneedles and a substrate.

DETAILED DESCRIPTION OF THE INVENTION

I. Definitions

"Analogue" as relates to a given compound, refers to another compound that is structurally similar, functionally similar, or both, to the specified compound. Structural similarity can be determined using any criterion known in the art, such as the Tanimoto coefficient that provides a quantitative measure of similarity between two compounds based on their molecular descriptors. Preferably, the molecular descriptors are 2D properties such as fingerprints, topological indices, and maximum common substructures, or 3D properties such as overall shape, and molecular fields. Tanimoto coefficients range between zero and one, inclusive, for dissimilar and identical pairs of molecules, respectively. A compound can be considered an analogue of a specified compound, if it has a Tanimoto coefficient with the specified between 0.5 and 1.0, inclusive, preferably between 0.7 and 1.0, inclusive, most preferably between 0.85 and 1.0, inclusive. A compound is functionally similar to a specified compound, if it induces the same pharmacological effect, physiological effect, or both, as the specified compound.

The terms "effective amount" or "therapeutically effective amount," as used herein, refer to a sufficient amount, preferably, of the drug (e.g., LT3 or salt thereof (e.g., an alkali salt thereof) being administered that would be expected to relieve to some extent one or more of the symptoms of the disease or condition being prevented, i.e., a quantity necessary to, for example, maintain a normal, stable serum total T3, free T3, free T3:free T4 ratio, total T3:free T4 ratio, and/or normalize serum TSH levels. The term "therapeutically effective amount" includes, for example, an "effective amount" of LT3 to achieve a desired pharmacologic effect; or maintain a stable serum level of total T3, free T3, free T3:free T4 ratio, total T3:free T4 ratio, and/or normalize serum TSH levels; without undue adverse side effects. Adverse side effects of over-treatment can include osteoporosis, cardiac arrhythmias, hair loss, bowel frequency, menstrual irregularities and psychosis. Adverse effects of under-treatment can include higher cholesterol levels, lower sense of well-being, lower basal metabolic rate resulting in weight gain, menstrual irregularities, and depression. It is understood that "an effective amount" or "a therapeutically effective amount" varies, in some implementations, from subject to subject, due to variation in metabolism of the compound administered, age, weight, general condition of the subject, the condition being prevented, the severity of the condition being prevented, and the judgment of the prescribing physician. It is also understood that "an effective amount" in an extended-release dosing format may differ from "an effective amount" in an immediate-release dosing format based upon pharmacokinetic and pharmacodynamic considerations.

The terms "triiodothyronine" (T3) and its synthetic form and pharmaceutical name, "liothyronine" (LT3), are used interchangeably. Likewise, "thyroxine" (T4) and the name of its synthetic form and pharmaceutical name, "levothyroxine" (LT4) are used interchangeably.

"GRAS" is an acronym for the phrase Generally Recognized as Safe. Under sections 201(s) and 409 of the US Federal Food, Drug, and Cosmetic Act (the Act), any substance that is intentionally added to food is a food additive, that is subject to premarket review and approval by FDA, unless the substance is generally recognized, among qualified experts, as having been adequately shown to be safe under the conditions of its intended use, or unless the use of the substance is otherwise excepted from the definition of a food additive. Under sections 201(s) and 409 of the Act, and FDA's implementing regulations in 21 CFR 170.3 and 21 CFR 170.30, the use of a food substance may be GRAS either through scientific procedures or, for a substance used in food before 1958, through experience based on common use in food Under 21 CFR 170.30(b), general recognition of safety through scientific procedures requires the same quantity and quality of scientific evidence as is required to obtain approval of the substance as a food additive. General recognition of safety through scientific procedures is based upon the application of generally available and accepted scientific data, information, or methods, which ordinarily are published, as well as the application of scientific principles, and may be corroborated by the application of unpublished scientific data, information, or methods. The database of compounds meeting the requirements defined by 21 CFR is found in Title 21: Food and Drugs, Part 184.

"Hypothyroidism" can be defined as a deficiency in the serum levels of endogenously produced thyroid hormone (Jonklaas, et al., Thyroid 2014, 24:1670-1751). Hypothyroidism can also occur when an individual has low levels of T4 and high levels of TSH as a result of a malfunctioning thyroid gland. For example, levels of TSH above 10 mIU/L with below normal levels of T4 evidence overt hypothyroidism (Garber, et al., Endocr. Pract. 2012, 18(6), 988-1028). Levels of total T3, free T4, free T3, and TSH can be determined from the serum of a patient, undergoing treatment or who has undergone treatment with the microneedle device, via standard analytical methods such as an enzyme-linked immunosorbent assay and radioimmunoassays (McAninch and Bianco, Ann. Intern. Med. 2016, 164:50-56; Conceiçao, et al., Thyroid 2018, 28(11), 1425-1433).

"Stable," as relates to serum levels of free or total T3 and/or free T4, refers to levels of one or both of these thyroid hormones that do not fluctuate above ±10% from a reference value within one hour, two hours, three hours, four hours, five hours, or 24 hours after administration. Both total T3 and free T3 can be measured. For example, the reference value can be a value within the range of what is considered normal levels of (i) free T3 in the serum when T3 levels are used, (ii) total T3 in the serum when T3 levels are used, (iii) free T4 in the serum when T4 levels are used, or (iv) TSH when serum TSH levels are used.

Appropriate medical ranges for TSH, T3, and T4, which would be considered normal, depends on where (Quest Diagnostics, LabCorp, Mayo Clinic, Abbott Architect, Beckman Coulter Unicel, Roche Cobas, Siemens Advia Centaur, etc.) and how it is measured (immunoassay or equilibrium dialysis/mass spec), as shown in the table below.

TABLE 1

Medical ranges for TSH, T3, and T4

|  |  | immunoassay | equilibrium dialysis and liquid chromatography/tandem mass spectrometry |
|---|---|---|---|
| Quest Diagnostics | TSH | 0.40-4.50 mIU/L |  |
|  | free T4 | 0.8-1.8 ng/dL | 0.9-2.2 ng/dL |
|  | free T3 | 2.3-4.2 pg/mL | 210-440 pg/dL |
|  | total T3 | 76-181 ng/dL | 76-181 ng/dL |
| Labcorp | TSH | 0.450-4.500 uIU/L |  |
|  | free T4 | 0.82-1.77 ng/dL | 0.8-1.7 ng/dL |
|  | free T3 | 2.0-4.4 pg/mL | 1.81-4.06 pg/mL |
|  | total T3 | 71-180 ng/dL | na |
| Mayo Clinic | TSH | 0.3-4.2 mIU/L |  |
|  | free T4 | 0.9-1.7 ng/dL | 0.8-2.0 ng/dL |
|  | free T3 | 2.8-4.4 pg/mL | na |
|  | total T3 | 80-200 ng/dL | na |

Table 2 of Barth, et al., Annals of Clinical Biochemistry 2018, 55(1), 107-112 also provides ranges for free T4 in pmol/L.

"Transdermal" refers to delivery across or into the epidermis, dermis, or both, wherein a component (e.g., a microneedle) of the delivery device (e.g. microneedle device) penetrates the epidermis, dermis, or both, but does not reach the subcutaneous connective tissue beneath the skin of a patient.

II. Microneedle Device

The microneedle device preferably includes at least two components: at least one, more preferably more, microneedle(s) and a substrate to which the base of the microneedle(s) are secured or integrated. The microneedle device, preferably, contains an effective amount of LT3 or a salt thereof (e.g., an alkali salt thereof) to maintain normal, stable levels, in the serum, of total or free T3; normalize levels of serum TSH; and/or maintain a normal serum free T3:free T4 ratio, or maintain normal serum total T3:free T4 ratio in a patient suffering from hypothyroidism, who is not a pregnant female. In some forms, the microneedle device contains LT3 or both LT3 and LT4, or a salt thereof). The LT3 and LT4, or salt thereof (e.g., an alkali salt thereof) can be in the same reservoir or microneedle, or in different reservoirs or microneedles of the same microneedle device.

The microneedle device can be a controlled release device, an immediate release device, or both. Preferably, the microneedle device is a controlled release device. Preferably, the amount of LT3 or salt thereof (e.g., alkali salt thereof) is effective in maintaining stable levels of serum free or total T3. It can be important to maintain stable levels of serum free T3, because these levels are typically kept from varying by less than 10% throughout a given day (Gullo, et al., PLoS One. 2011; 6:e22552; Peterson, et al., J. Clin. Endocrinol. Metab. 2016, 101(12):4964-4973; Conceiçao, et al., Thyroid 2018, 28(11), 1425-1433).

Further, maintaining normal serum free (or total) T3:free T4 ratio can be an important consideration in the delivery of thyroid hormones, because higher serum levels of T4 can impair systemic T3 production by downregulating a deiodinase pathway (McAninch and Bianco, Ann. Intern. Med. 2016, 164:50-56). The serum free T3:free T4 ratio in a study of about 3800 healthy individuals was about 0.32 (0.27-0.37, 95% CI) (Gullo, et al., PLoS One. 2011; 6:e22552). In another population study of about 9,700 healthy individuals the free T3:free T4 ratio was 0.41±0.09 and the total T3:free T4 ratio was 149.6±40.7 (Peterson, et al., J. Clin. Endocrinol. Metab. 2016, 101(12):4964-4973). Therefore, in some forms, based on the studies reported in Peterson, et al., J. Clin. Endocrinol. Metab. 2016, 101(12):4964-4973 and Gullo, et al., PLoS One. 2011; 6:e22552, the LT3 is effective in maintaining a serum free T3:free T4 ratio of about 0.32, 0.41±0.09, between about 0.27 and about 0.37, between 0.27 and 0.42, inclusive, between about 0.30 and about 0.42, or between 0.37 and 0.42, inclusive.

In some forms, the microneedle(s) are biodegradable and/or dissolvable, and contains the drug (e.g. LT3 or salt thereof (e.g. alkali salt thereof)) that is being delivered to the patient.

As a controlled release microneedle device, the microneedle(s) contain LT3 or both LT3 and LT4, or a salt thereof, and a biodegradable and/or dissolvable polymer, such as polyvinylpyrrolidone. The LT3 and LT4 can also be provided in their salt form, such as an alkali salt.

As a controlled release microneedle device, the microneedle(s) release LT3 or both LT3 and LT4 or a salt thereof, such that dosing (e.g., application of a microneedle device) can be performed every eight hours, daily, every other day, twice weekly, every week, once every 28 to 31 days, or a maximum of every three months, depending on the indication.

As a controlled release microneedle device, the microneedle(s) contain (i) LT3 or both LT3 and LT4, or a salt thereof, and a biodegradable and/or dissolvable polymer, such as polyvinylpyrrolidone, and (ii) the microneedle(s) release LT3 or both LT3 and LT4, or salt thereof, such that dosing (e.g., application of a microneedle device) can be performed every eight hours, daily, every other day, twice weekly, every week, once every 28 to 31 days, or a maximum of every three months, depending on the indication.

Preferably, the release follows zero-order release kinetics, with minimal to no burst release.

In some forms, the microneedle device further contains at least one reservoir that is not a microneedle, which is in connection (selectably in fluid connection) preferably with the base end of at least one of the microneedles, either integrally or separably until the moment of use. In these forms, the reservoir contains the drug (e.g., LT3, or LT3 and LT4, and/or a salt thereof).

Preferably, the microneedles are provided as a multidimensional array, in contrast to a microneedle device with a single microneedle or single row of microneedles. The microneedle devices can be adapted to be a single-use, disposable device, or can be adapted to be fully or partially reusable.

Drugs

Preferably, LT3 is delivered with the microneedle device. The LT3 can be provided in its salt form, such as an alkali salt. Other drugs to be delivered can also be provided in their salt form. The amount of LT3 or a salt thereof can be selected by one of skill in the art, based, for example, on the desired effect of LT3 or salt thereof at the planned release levels, and the time span over which the LT3 or salt thereof should be released. In some forms, LT3 or salt thereof in the microneedle device is in a quantity to provide an effective amount of LT3 or salt thereof to a subject in need thereof. For example, for an average 70-kg adult, effective amounts can be between 2.5 μg and 45 μg, inclusive, of LT3/day, between 5 μg and 20 μg, inclusive, of LT3/day, or between 5 μg and 10 μg, inclusive, of LT3/day. Where the microneedle(s) serve as reservoirs for LT3, or both LT3 and LT4, or salt thereof, the daily amount can depend on the biodegradable and/or dissolvable polymer, the presence of low molecular weight generally recognized as safe (GRAS) organics, the release kinetics of LT3 and/or LT4, salt thereof, or a combination of these. "Low molecular weight" refers to a compound, preferably, non-polymeric compound, that has a molecular weight between 200 Da and 2,500 Da, inclusive.

Further, other drugs can be delivered together with LT3 or salt thereof using these microneedle devices. As used herein, the term "drug" refers to a compound that possesses therapeutic, prophylactic, or diagnostic properties in vivo, for example when administered to an animal, including mammals, such as humans. The therapeutic, diagnostic, and/or prophylactic agents can be peptides, proteins, carbohydrates, nucleic acids, lipids, organic molecules, biologically active inorganic molecules, and combinations thereof. Examples of suitable therapeutic and/or prophylactic active agents include non-peptide hormones including LT4, analogues of thyroid hormones, such as LT4 or LT3 N-methyl, LT4 or LT3 N-ethyl, LT4 or LT3 N-triphenyl, LT4 or LT3 N-propyl, LT4 or LT3 N-isopropyl, LT4 or LT3 N-tertiary butyl, 3,5-dimethyl-4-(4'-hydroy-3'-isopropylbenzyl)-phenoxy acetic acid (GC-I), 3,5-diiodothyropropionic acid (DITPA), tetraiodothyroacetic acid (TETRAC), and triiodothyroacetic acid (TRIAC), sobetirome, eprotirome, MB07811/VK2809, MGL-3196, T2, T1AM, TA1, or salts thereof; antibiotics; steroids; neuroactive agents; anesthetics; and sedatives. Examples of suitable diagnostic agents include radioactive isotopes; radioopaque agents; metals; gases; and labels including chromatographic, fluorescent, or enzymatic labels.

Microneedles

Solid Microneedles

In some forms, the microneedle(s) are solid. "Solid," in this context, means that a microneedle does not contain an annular bore or channel from its base to its apex. In these forms, the microneedle(s) can serve as reservoir(s) for a drug (e.g., LT3, or LT3 and LT4, or salt thereof) that is being delivered to a patient. Preferably, in these forms, the microneedles are made from biodegradable and/or biodissolvable compounds, such as polymers, low molecular weight GRAS organics, or a combination of these. In these forms, the microneedles can include GRAS inert excipients or additives. These excipients may enhance incorporation of a drug into the microneedle(s), control the rate of degradation of the microneedle(s), influence the release kinetics of a drug, or a combination thereof.

Preferably, when the microneedle(s) serve as reservoir(s) for a drug (e.g., LT3, or LT3 and LT4, or a salt thereof) that is being delivered to a patient, the microneedle device can be applied to the skin, and the substrate separated from the microneedles, leaving the microneedles embedded in the skin for the controlled release of the drug (e.g., LT3, or LT3 and LT4, or a salt thereof). Accordingly, the microneedle device can include means than facilitates separating the substrate from the microneedles. The means can be a joint, a bubble, or a combination thereof, between a microneedle(s) and the substrate.

Hollow Microneedles

The microneedles can be hollow; that is, each containing at least one substantially annular bore or channel having a diameter large enough to permit passage of a drug-containing fluid and/or solid materials through the microneedle. The hollow shafts may be linear, i.e., extend upwardly from needle base to needle tip, or they may take a more complex path, e.g., extend upwardly from the needle base, but then lead to one or more 'portholes' or 'slits' on the sides of the needles, rather than an opening at the needle tip. Where the microneedle device contains a hollow microneedle, the microneedle device can also contain a means for stopping delivery of the drug (e.g., LT3, or LT3 and LT4, or a salt thereof). The microneedle device can also contain a rate control means, which can be used to regulate the rate or extent at which materials flow through the microneedles. In some forms, the rate control means is in the microneedles.

The microneedles can be constructed from biodegradable and/or biodissolvable materials, or non-biodegradable materials. Non-biodegradable materials include metals, ceramics, semiconductors, non-biodegradable organic compounds (such as non-biodegradable polymers), and composites. Some specific non-biodegradable materials include pharmaceutical grade stainless steel, gold, titanium, nickel, iron, tin, chromium, copper, palladium, platinum, alloys of these or other metals, silicon, silicon dioxide, polymers with carbon backbones such as polystyrenes and polyolefins. "Composites" is a term of art and refers to materials containing two or more different materials, associated with each other via physical, non-covalent interactions. Thus, composites can include metal alloys as well as mixtures of non-metallic materials. Representative biodegradable and/or biodissolvable materials include low molecular weight GRAS organic compounds; and polymers. The polymers include polyvinyl pyrrolidone, polyvinyl alcohol, polymers of hydroxy acids such as polylactide, polyglycolide, polylactide-co-glycolide, and their copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides. Other dissolvable materials include sugars.

The microneedles should have the mechanical strength to remain intact while being inserted into the biological barrier, while remaining in place for up to a number of days, and, if applicable, while being removed.

In preferred embodiments the microneedles are formed of biodegradable and/or biodissolvable compounds (such as biodegradable and/or biodissolvable polymers). These microneedles must remain intact at least long enough for the microneedle to be inserted into the patient.

The microneedles should be sterilizable using standard methods such as ethylene oxide or gamma irradiation.

The microneedles can have straight or tapered shafts. In a preferred form, the diameter of the microneedle is greatest at the base end of the microneedle and tapers to a point at the end distal the base. The microneedle can be fabricated to have a shaft that includes both a straight (untapered) portion and a tapered portion. The needles may not have a tapered end at all, i.e., they may simply be cylinders with blunt or flat tips. A hollow microneedle that has a substantially uniform diameter, but which does not taper to a point, is referred to herein as a "microtube." Microneedles can also include a groove on the side to direct agent from a reservoir in the substrate into the tissue at the point of insertion. As used herein, the term "microneedle" includes both microtubes and tapered needles unless otherwise indicated.

The microneedles can be oriented perpendicularly or at an angle to the substrate. Preferably, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g., star-shaped, square, triangular), oblong, or another shape. The shaft can have zero, one or more bores. The cross-sectional dimensions typically are between about 1 µm and 500 µm, and preferably between 10 and 100 µm. The outer diameter is typically between about 10 µm and about 100 µm, and the inner diameter is typically between about 3 µm and about 80 µm.

In one form the cross-sectional dimensions are designed to leave a residual hole (following microneedle insertion and withdrawal) of less than about 0.2 µm, to avoid making a hole which would allow bacteria to enter the penetration wound. The actual microneedle diameter will typically be in the few micron range, since the holes typically contract following withdrawal of the microneedle. Larger diameter and longer microneedles are acceptable, so long as the microneedle can penetrate the biological barrier to the desired depth.

The length of the microneedles typically is between about 10 µm and 1 mm, such as between 100 µm and 700 µm, between 100 µm and 600 µm, between 100 µm and 500 µm, or between 150 µm and 350 µm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In transdermal applications, the "insertion depth" of the microneedles is preferably less than about 100 µm to 700 µm, or less than about 100 µm to 600 µm, so that insertion of the microneedles into the skin does not penetrate into the dermis, thereby avoiding contacting nerves which may cause pain. In such applications, the actual length of the microneedles typically is longer, since the portion of the microneedles distal the tip may not be inserted into the skin; the uninserted length depends on the particular device design and configuration. The actual (overall) height or length of microneedles should be equal to the insertion depth plus the uninserted length.

The microneedles typically have a gauge size of between 26 Gauge and 31 Gauge, inclusive, between 26 Gauge and 32 Gauge, inclusive, between 26 Gauge and 33 Gauge, inclusive, or between 26 Gauge and 34 Gauge, inclusive. Exemplary gauge sizes include 26 Gauge, 27 Gauge, 28 Gauge, 29 Gauge, 30 Gauge, and 31 Gauge.

Substrate

The substrate of the microneedle device can be constructed from a variety of materials, including metals, ceramics, semiconductors, organics, polymers, and composites. The substrate includes the base to which the microneedles are attached or integrally formed. The substrate can be adapted to fit a Luer-Lock syringe or other conventionally used drug delivery device that currently uses hypodermic needles as the barrier penetration method.

In some forms of the microneedle device, the substrate, as well as other components, are formed from flexible materials to allow the microneedle device to fit the contours of the biological barrier, such as the skin, to which the microneedle device is applied. A flexible microneedle device may facilitate more consistent penetration of some biological barriers, because penetration can be limited by deviations in the attachment surface. For example, the surface of human skin is not flat due to dermatoglyphics (i.e., tiny wrinkles) and hair. However, for some biological barriers, a rigid substrate may be preferred.

Reservoir

The reservoir is selectably in connection with the microneedle bore, such that the reservoir contents can flow from the reservoir and out through the microneedle tip, into the target tissue. Typically, it is attached to, or integrated into, the substrate, either integrally (as in a one-piece device) or at the moment of drug delivery (as with a Luer-lock type device). The reservoir is to provide suitable, leak-free storage of the drug composition before it is to be delivered. The reservoir should keep the drug composition free of contaminants and degradation-enhancing agents. For example, the reservoir should exclude light when the drug composition contains photo-sensitive materials, and should include an oxygen barrier material in order to minimize exposure of drugs sensitive to oxidation. Also, the reservoir should keep volatile materials inside the reservoir, for example, to prevent water from evaporating, causing the drug composition to dry out and become undeliverable.

The drug reservoir can be substantially rigid or readily deformable. The reservoir can be formed from one or more polymers, metals, ceramics, or combinations thereof. In a preferred form, the reservoir includes a volume surrounded by one or more walls, or includes a porous material, such as a sponge, which can retain, for example, the drug liquid until the material is compressed.

In a preferred form, the reservoir is formed of an elastic material, such as an elastomeric polymer or rubber. For example, the reservoir can be a balloon-like pouch that is stretched (in tension) when filled with a fluid drug composition to be delivered.

Figure 4A:
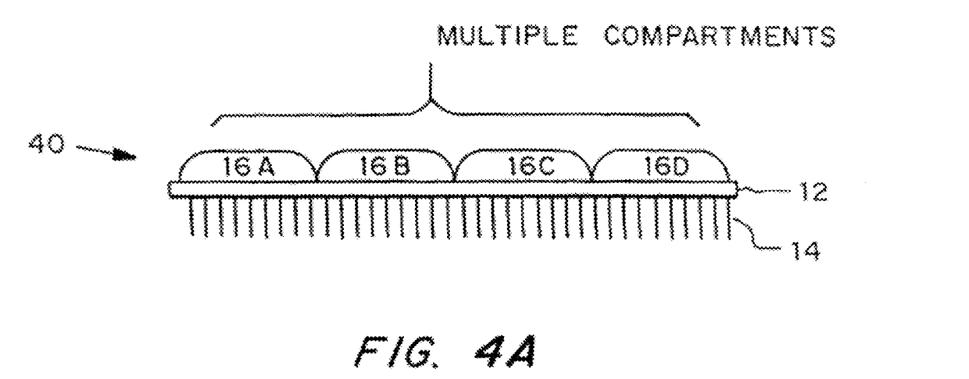
FIGS. 4A and 4B are cross-sectional views of a microneedle device having a multiple chambered reservoir.
Figure 4B:
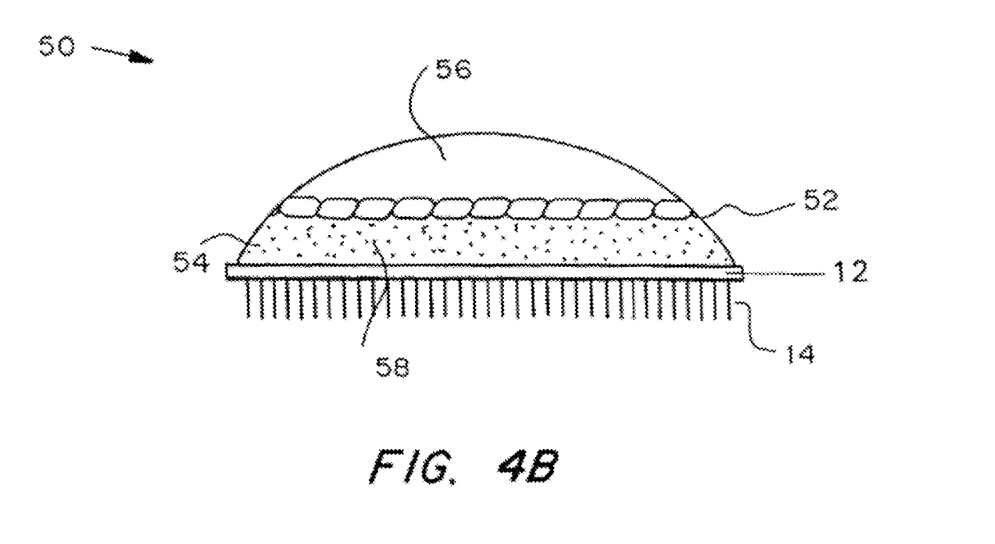

The reservoir of a single microneedle device can include a plurality of compartments that are isolated from one another and/or from a portion of the microneedles in an array. The microneedle device can, for example, be provided to deliver different drugs through different needles, or to deliver the same or different drugs at different rates or at different times (FIG. 4A). Alternatively, the contents of the different compartments can be combined with one another, for example, by piercing, or otherwise removing, a barrier between the compartments, so as to allow the materials to mix. In a preferred form, one compartment contains a saline solution or another delivery vehicle, while another compartment contains lyophilized drug (FIG. 4B). In a preferred form, the reservoir is a standard or Luer-Lock syringe adapted to connect to a microneedle array.

III. Methods of Making

The microneedle and substrate are made by methods known to those skilled in the art. Examples include microfabrication processes, by creating small mechanical structures in silicon, metal, polymer, and other materials. Three-dimensional arrays of hollow microneedles can be fabricated, for example, using combinations of dry etching processes; micromold creation in lithographically-defined polymers and selective sidewall electroplating; or direct micromolding techniques using epoxy mold transfers. These methods are described, for example, in U.S. Ser. No. 09/095,221, filed Jun. 10, 1998; U.S. Ser. No. 09/316,229, filed May 21, 1999; Henry, et al., "Micromachined Needles for the Transdermal Delivery of Drugs," *Micro Electro Mechanical Systems*, Heidelberg, Germany, pp. 494-98 (Jan. 26-29, 1998).

A non-limiting example of making three-dimensional arrays of solid microneedles is described in Li, et al., Nat. Biomed. Eng. 2019, 3, 220-229. The method generally involves applying a substrate to an array of separable microneedles that can controllably release a drug (e.g., LT3, or LT3 and LT4), over a desired time. The substrate, after formation, can contain an array of pedestals positioned at the base of each microneedle to elevate the microneedles above the base of the substrate.

Briefly, a suitable mold (such as a polydimethylsiloxane mold) can be used to template the microneedles for making the microneedle device. The microneedles can be arranged in a desired array, center-to-center interval, and area. The microneedles can have straight shafts, tapered shafts, or a combination of these.

Microneedle device fabrication can involve casting one or more solutions onto the mold. Preferably, at least one solution contains the drug (e.g., LT3, or LT3 and LT4, or a salt thereof) and the biodegradable and/or biodissolvable compound (such as a biodegradable and/or biodissolvable polymer, e.g., polyvinyl pyrrolidone). The concentration of the solution can be selected, such that the biodegradable and/or biodissolvable compound exerts primary control over the drug release rate.

Where needed, a second casting solution containing a polymer (such as polyvinyl alcohol), and optionally another compound (such as sucrose), in a solvent such as deionized water, can be applied to the mold surface to form part or all of the substrate. During this casting, an air bubble can be trapped between the microneedle and the pedestal of the substrate. The bubble size can be controlled by adjusting the volume of the second casting solution. After drying (such as in a chemical hood) the mold can be further placed in a desiccator at room temperature, for complete drying, if needed. The formed microneedle device can be carefully peeled from the mold and safely stored (e.g., in a desiccator) for later use.

IV. Methods of Using

The preferred patient population for the microneedle device includes patients suffering from hypothyroidism, who are not pregnant. It is not advisable to give LT3 to pregnant women, because T3 does not cross the placenta in adequate doses. The placenta expresses a large amount of a deiodinase that inactivates T3 (Jonklaas, et al., Thyroid 2014, 24:1670-1751). The fetal thyroid gland does not start making sufficient thyroid hormone until about 18-20 weeks gestation, so the fetus is dependent on maternal thyroid hormone in early pregnancy. If enough thyroid hormone is not available, this can cause growth and developmental delay, a clinical syndrome that can be known as cretinism in its most severe form. However, it should be noted that an LT4 in the microneedle device would be acceptable for pregnant women, given that LT4 crosses the placenta.

The microneedle device is applied to the skin of a patient in need thereof, to maintain normal levels of serum TSH, serum free or total T3, and/or serum free (or total) T3: free T4 ratio in the patient. Preferably, the microneedle device contains LT3 or salt thereof. Preferably, the patient has hypothyroidism. Than, et al., Small Methods 2017, 1, 1700269 described transdermal delivery of anti-obesity compounds, including LT3, to convert white adipose tissue to brown adipose tissue as a strategy to treat obesity. However, the patient population and/or the test mice models described in Than, et al., Small Methods 2017, 1, 1700269 were only obese and not hypothyroid.

The LT3 or salt thereof in the microneedle device can be administered in a single dose or in multiple doses. The LT3 or salt thereof can also be formulated to be administered as an immediate release or controlled release formulation. Certain factors may influence the dosage required to effectively treat or ameliorate hypothyroidism, including, but not limited to, the severity of the disease or disorder, previous preventions, the general health and/or age of the subject, and other diseases present. It will also be appreciated that the effective dosage of the formulation used for treatment may increase or decrease over the course of a particular treatment. Changes in dosage may result and become apparent from the results of assays.

In some forms, a reservoir of the microneedle device contains LT3 or salt thereof formulated alone in a pharmaceutically acceptable excipient and delivered to a patient in need thereof.

In other forms, a reservoir of the microneedle device contains LT3 or salt thereof formulated alone in a pharmaceutically acceptable excipient, and is administered in combination with LT4 or salt thereof in a combination therapy. In these forms, LT3 or salt thereof is used for supplementation in patients taking LT4 or salt thereof. In this 'combination therapy' regimen, the LT4 or salt thereof can be administered orally, transdermally, or both. When LT4 or salt thereof is administered orally, LT4 or salt thereof can be in the form of an oral solution, tablet, or pill. When LT4 or salt thereof is administered transdermally, LT4 or salt thereof can be administered via the same microneedle device that contains LT3 or salt thereof or in another microneedle device that optionally does not contain LT3 or salt thereof. When LT3 and LT4, or salt thereof, are administered via the same microneedle device, LT3 and LT4, or salt thereof can be in the same reservoir or in different reservoirs of the same microneedle device.

Other Additives and Excipients

The microneedle device can also include other additives and/or excipients.

These additives and/or excipients can be incorporated into the microneedle(s). Preferably, these are GRAS organics. Representative GRAS organics that are non-ionic. These include polysaccharides (such as cellulose); low molecular weight GRAS compounds, such as ascorbyl alkanoate, sorbitan alkanoate, triglycerol monoalkanoate, sucrose alkanoate, glycocholic acid, retinyl acetate, and alpha-tocopherol acetate; or a combination of these. The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can be ascorbyl palmitate, ascorbyl decanoate, ascorbyl laurate, ascorbyl caprylate, ascorbyl myristate, ascorbyl oleate, or any combination thereof. The sorbitan alkanoate can be sorbitan monostearate, sorbitan decanoate, sorbitan laurate, sorbitan caprylate, sorbitan myristate, sorbitan oleate, or any combination thereof. The triglycerol monoalkanoate can include triglycerol monopalmitate, triglycerol monodecanoate, triglycerol monolaurate, triglycerol monocaprylate, triglycerol monomyristate, triglycerol monostearate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof.

In some forms, the additives and/or excipients can be incorporated into a formulation containing LT3 or salt thereof. In some forms, these other materials are in a separate reservoir from that containing LT3 or salt thereof. Representative materials include chemical permeation enhancers (CPEs), diluents, buffers, dispersing agents or viscosity modify agents, and stabilizers. Preferably, these additives and excipients do not cause problems such as skin irritation, discomfort, and/or sensitization.

Representative classes of CPEs include, but are not limited to, a fatty acid, terpene, fatty alcohol, a medium chain glyceride, a surfactant, a steroidal detergent, pyrrolidine, sulfoxide, laurocapram, amide, amine, quaternary ammonium compound, silicone, alkanoate, an acyl carnitine, lauroyl-DL-carnitine, an alkanoyl choline, an N-acetylated amino acid, esters, salts, bile salts, sodium salts, nitrogen-containing rings, derivatives thereof, and combinations thereof. The CPE can be anionic, cationic, zwitterionic, or nonionic. Anionic CPEs can include, but are not limited to, sodium lauryl sulfate, sodium decyl sulfate, sodium octyl sulfate, N-lauryl sarcosinate, and sodium carparate. Cationic CPEs can include, but are not limited to, cetyltrimethyl ammonium bromide, decyltrimethyl ammonium bromide, benzyldimethyl dodecyl ammonium chloride, myristyltimethyl ammonio chloride, and deodecyl pridinium chloride. Zwitterionic CPEs can include, but are not limited to, decyldimethyl ammonio propane sulfonate, palmityldimethyl ammonio propane sulfonate. Fatty acids can include, but are not limited to, butyric, caproic, caprylic, pelargonic, capric, lauric, myristic, palmitic, stearic, arachidic, oleic, linoleic, and linolinic acid, salts thereof, derivatives thereof, and combinations thereof. In some forms, a fatty acid may be modified as an ester, for example, a glyceride, a monoglyceride, a diglyceride, or a triglyceride. Bile acids or salts including conjugated or unconjugated bile acid CPEs can include, but are not limited to, cholate, deoxycholate, taurocholate, glycocholate, taurodexycholate, ursodeoxycholate, tauroursodeoxycholate, chenodeoxycholate, derivates thereof, salts thereof, and combinations thereof. In some forms, CPEs can comprise a metal chelator, such as EDTA or EGTA, a surfactant such as sodium dodecyl sulfate, polyethylene ethers or esters, polyethylene glycol-12 lauryl ether, salicylate polysorbate 80, nonylphenoxypolyoxyethylene, dioctyl sodium sulfosuccinate, saponin, palmitoyl carnitine, lauroyl-1-carnitine, dodecyl maltoside, acyl carnitines, alkanoyl cjolline, and combinations thereof. Other CPEs can include, but are not limited to, 3-nitrobenzoate, zoonula occulden toxin, fatty acid ester of lactic acid salts, glycyrrhizic acid salt, hydroxyl beta-cyclodextrin, N-acetylated amino acids such as sodium N-[8-(2-hydroxybenzoyl) amino]caprylate and chitosan, salts thereof, derivatives thereof, and combinations thereof. An exemplary CPE is 1% by weight palmityldimethyl ammonio propane sulfonate (PPS). CPEs are also described in Whitehead et al., J. Control. Release, 128 (2008) 128-133 and in Whitehead et al., Pharm. Res., 25 (2008) 1782-1788, the entire contents of which are incorporated herein by reference.

The term "diluent" refers to chemical compounds that are used to dilute, preferably, the formulation containing LT3 or salt thereof prior to delivery, and which are compatible, preferably, with the epidermis and/or dermis.

The term "dispersing agents," and/or "viscosity modulating agents" and/or "thickening agents" refer to materials that control the diffusion and homogeneity, preferably, of the formulation in the reservoir through liquid media. Examples of dispersing agents/materials that control diffusion include, but are not limited to, hydrophilic polymers, electrolytes, TWEEN® 60 or TWEEN® 80, PEG, polyvinylpyrrolidone (PVP; commercially known as PLASDONE®), and the carbohydrate-based dispersing agents such as, for example, modified celluloses such as hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), and polyethylene glycol.

The formulation containing LT3 or salt thereof in the reservoir can have a viscosity suitable for flowing through a microneedle having a gauge size between 26 Gauge and 31 Gauge, inclusive, between 26 Gauge and 32 Gauge, inclusive, between 26 Gauge and 33 Gauge, inclusive, or between 26 Gauge and 34 Gauge, inclusive.

The term "stabilizer" refers to compounds such as any buffers, acids, and preservatives that are compatible, preferably, with the environment of the epidermis and dermis. Stabilizers include compounds that improve the compatibility of excipients with a reservoir, or a microneedle, improve the stability of a component of the formulation, or improve formulation stability.

V. Illustrative Microneedle Devices

EXAMPLES

Illustrative forms of the microneedle device are shown in FIGS. 1A-1C. The microneedle device 10 includes substrate 12 from which a three-dimensional array of microneedles 14 protrude. As shown, the annular bore of the microneedles 14 extends through the substrate 12. The microneedle device 10 also includes a reservoir 16 secured to substrate 12 via a sealing mechanism 18. FIG. 1A shows how the reservoir can be accessed directly by application to the skin, for example, for simple transdermal delivery of an agent. The microneedle device in FIG. 1B includes a deformable bubble reservoir 16. Manual pressure can be used to expel its contents at the site of application. FIG. 1C shows a separate reservoir 16 from means 19 for expelling the contents of the reservoir 16 at the site of administration. The expelling means 19 can be simply a flexible bag. The expelling means 19 may also contain a vacuum so that it expands when vented, to create pressure on the reservoir, or it may be elastic so that it deforms when released from one position (not shown). Alternatively, reservoir 16 could be formed of an elastic material which deforms when released.

The sealing mechanism 18 can be, for example, an adhesive material or gasket. The sealing mechanism 18 can further function as or include a fracturable barrier or rate controlling membrane overlaying the surface of the substrate. In this form, nothing can be released until a seal or peel-off strip covering is removed.

Figure 2:
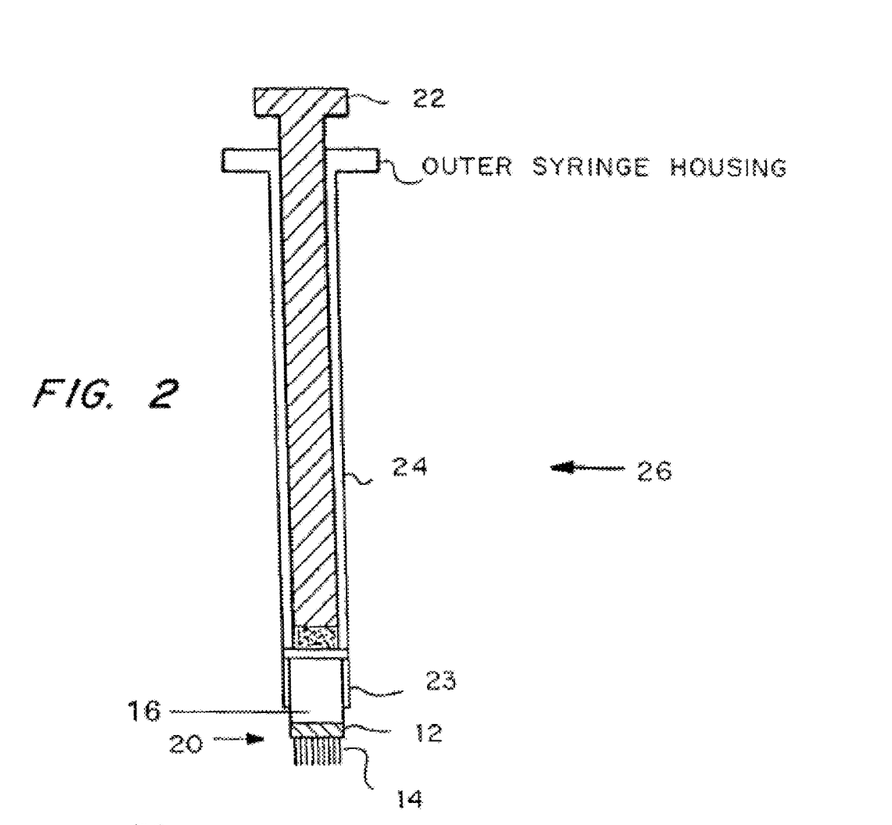
FIG. 2 is a cross-sectional view of another microneedle device, wherein delivery is activated by manual pressure applied via a plunger to compress the reservoir.

Another form of the microneedle device is shown in FIG. 2. The microneedle device 20 includes substrate 12 from which a three-dimensional array of microneedles 14 protrude. The microneedle device 20 also includes plunger 22 that is slidably secured to the upper surface of substrate 12 by plunger guide frame 24 using a restraint such as a Leur-lock interface 23. The substrate 12 can be attached or detached to a syringe 26 via a connector such as a Luer-lock type attachment 23. The plunger 22, guide frame 24, and connector 23 connect to, form or contain reservoir 16. A Luer-lock type attachment could alternatively be used to secure the microneedle device to means for controlling flow or transport through the microneedle device such as a pump.

Figure 3:
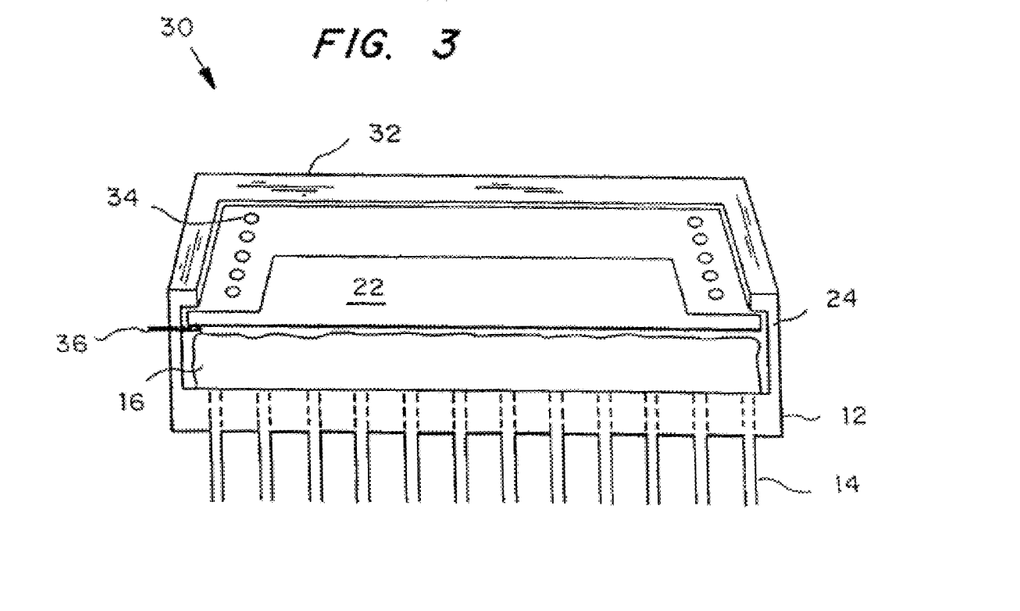
FIG. 3 is a cross-sectional view of another microneedle device, wherein delivery is activated by releasing a compressed spring which forces the plunger to compress the reservoir.

A further preferred form of the microneedle device is shown in FIG. 3. Like the microneedle device in FIG. 2, the microneedle device 30 includes substrate 12, microneedles 14, plunger 22, plunger guide frame 24, and reservoir 16. The microneedle device 30 further includes plunger housing 32, which is attached to, or integrally formed with, plunger guide frame 24. A compressed spring or other tension-based mechanism 34 is positioned between plunger housing 32 and plunger 22. The microneedle device 30 further includes spring hold/release mechanism 36, which keeps the plunger up (spring compressed) until triggered to compress reservoir 16.

Attachment Feature

In some forms, the microneedle device includes an adhesive material to secure the microneedle device to the skin, temporarily immobilizing the microneedles while inserted into the skin to deliver the drug. The adhesive agent typically is applied to the substrate (in between the microneedles at their base) or to an attachment collar or tabs adjacent the microneedles.

Care must be taken so that any adhesive agent does not plug the bores of hollow microneedles. For example, the adhesive agent can be applied in a liquid solution by flooding the top of the substrate below the tips of the microneedles, such as from the side of an array of microneedles, or by using a three-dimensional printing process. The solvent can then be evaporated from the adhesive agent solution, thereby precipitating or gelling the adhesive agent to yield a tacky surface. An alternate method of keeping the tips free of an applied adhesive agent is to choose materials of construction having a hydrophobicity or hydrophilicity to control the wetting of the surface to the microneedle tips.

Initiating Delivery

Figure 1A:
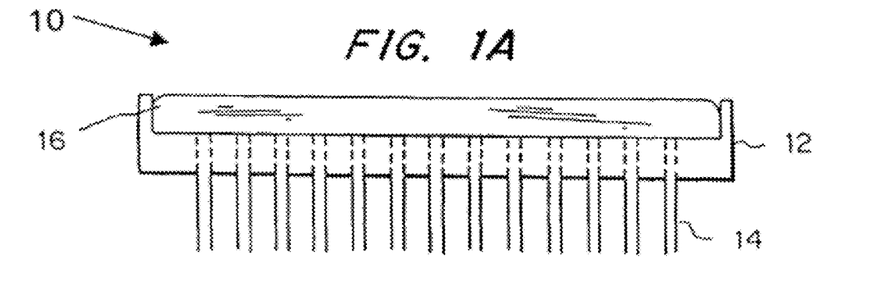
FIGS. 1A-1C are cross-sectional views of a microneedle device. The microneedle device of FIG. 1A includes a reservoir and is suitable for transdermal drug delivery. The microneedle device of FIGS. 1A and 1B includes a deformable reservoir, wherein delivery is activated by manual, e.g., finger or thumb, pressure applied to compress the reservoir directly (FIG. 1B) or indirectly (FIG. 1C).
Figure 1B:
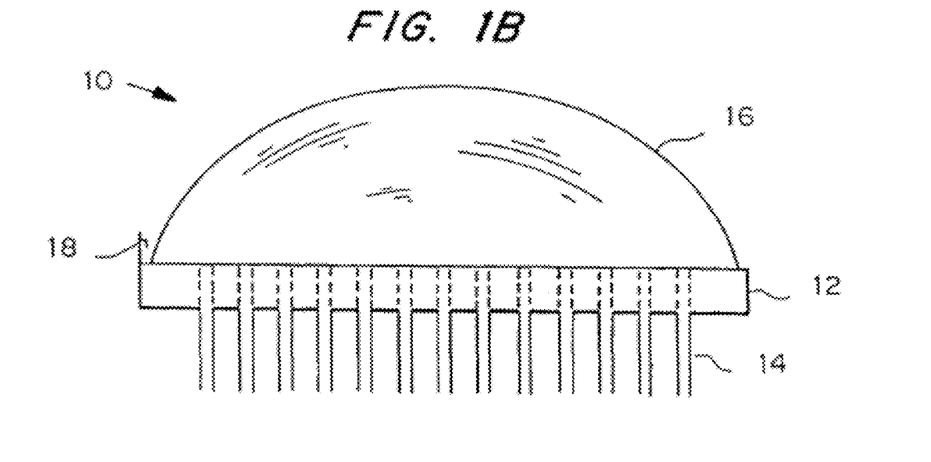
Figure 1C:
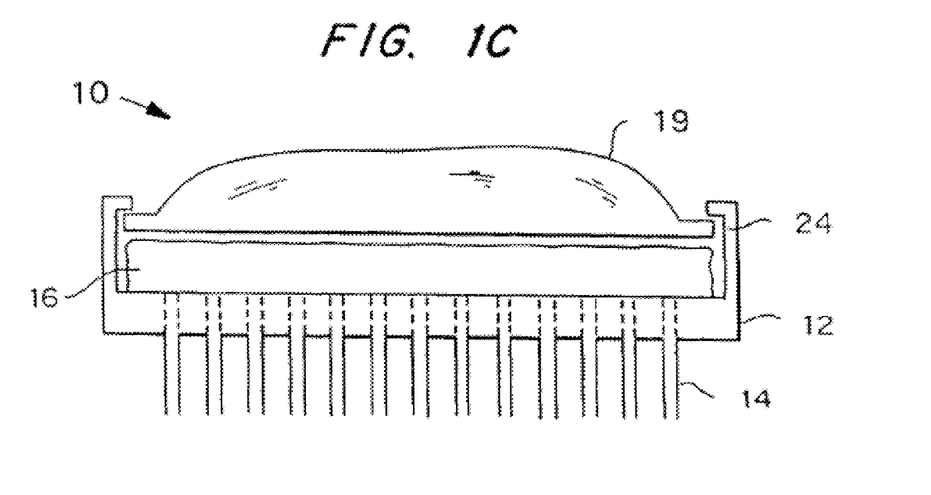

In some forms, delivery of the drug from the reservoir is initiated by applying a force, such as by pressing the top of the reservoir, to cause the reservoir contents (i.e., a drug containing composition) to flow out through the microneedles—an active or dynamic process. For example, the user can apply finger-pressure directly to a deformable reservoir "bubble," (FIGS. 1A-1C) or to a plunger mechanism (FIG. 2) or a Luer-lock type syringe that in turn causes the drug composition to be forced from the reservoir. The plunger also can be adapted to activate by application of a constant, reproducible force, for example, a spring (e.g., under compression) (FIG. 3) or elastic band (e.g., in tension).

A variation of this form utilizes a balloon-like reservoir in tension to provide the force. Then, when an opening is formed in the balloon reservoir, the contents are forced out of the reservoir as the balloon contracts to its relaxed state. The contraction is selectively triggered to provide the driving force for delivery.

In some forms, the force ruptures a fracturable barrier between the reservoir contents and the inlet of the microneedle. Representative barriers include thin foil, polymer, or laminant films. In another form, the microneedles tips are blocked until immediately before use. The blocking material can be, for example, a peelable adhesive or gel film, which will not clog the openings in the microneedle tip when the film is removed from the microneedle device.

Delivery also can be initiated by opening a mechanical gate or valve interposed between the reservoir outlet and the microneedle inlet. For example, a thin film or plate can be slid or peeled away from the back of the substrate.

In an alternate form, delivery is initiated by changing the physical or chemical properties of the drug composition and/or of a barrier material. For example, the barrier can be a porous membrane having a porosity that can be selectably altered to permit flow, or the drug composition can be selected to change from a solid or semi-solid state to a fluid state, for example as the temperature is increased from ambient to that of body temperature. Such a drug composition can be prepared, for example, by combining the drug with a biodegradable polymeric material.

Another form of the microneedle device is shown in FIG. 4A. FIG. 4A shows microneedle device 40 in which microneedles 14 attached to a substrate 12 which is attached to multiple compartments 16a, 16b, 16c, and 16d. Each compartment can contain or function as a reservoir. Material can be expelled from each compartment through all or a subset of microneedles 14.

FIG. 4B depicts a microneedle device 50 in which microneedles 14 are attached to a substrate 12 which is attached to reservoir 58 containing, for example, lyophilized drug 54. The reservoir 58 is attached to a fracturable barrier 52 which is attached to another reservoir 56 containing, for example, saline. If the barrier 52 is fractured, then the two reservoirs 54 and 56 are in fluid communication with each other and their contents can mix.

Delivery also can be initiated by activating an osmotic pump, as described, for example, in U.S. Pat. No. 4,320,758 to Eckenhoff, which has been adapted to the substrate of the microneedle device. For example, the reservoir/osmotic pump includes an inner flexible bag that holds the drug charge, an intermediate layer of an osmotically effective solute composition, such as an inorganic salt, that encapsulates the bag, and an outer shape-retaining membrane that is at least in part permeable to water and that encapsulates both the layer of osmotically effective solute composition and the bag. In operation, the bag filled with the fluid drug compositions is exposed to an aqueous environment, so that water is imbibed from the environment by the osmotically effective solute through the membrane into the space between the inner flexible bag and the membrane. Since the bag is flexible and the membrane is rigid, the imbibed water squeezes the bag inwardly, thereby displacing drug out the microneedles.

Figure 5:
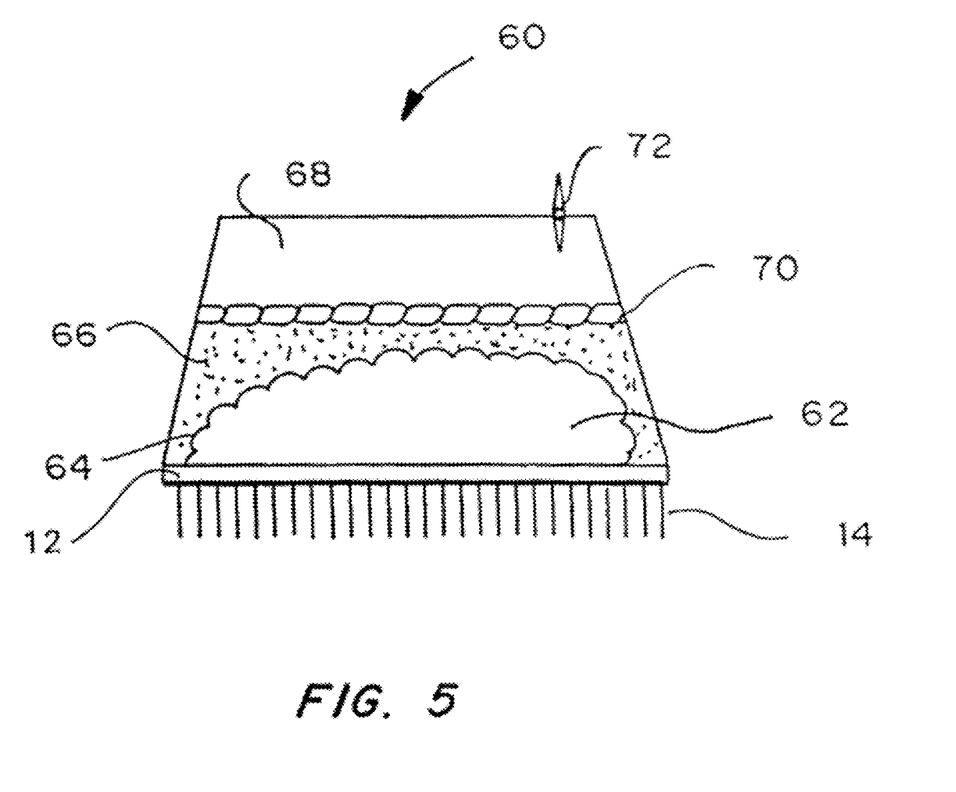
FIG. 5 is a cross-sectional view of a microneedle device, which incorporates an osmotic pump to force the drug contents from the reservoir.

FIG. 5 shows a microneedle device 60 in which microneedles 14 are attached to a substrate 12 which is attached to a drug reservoir 62. This reservoir is surrounded at least partially by a flexible, impermeable membrane 64. The drug reservoir is connected to another reservoir 66 which contains, for example, an inorganic salt. The two reservoirs 62 and 66 are separated by the impermeable membrane 64, which is impermeable to the contents of both reservoirs 62 and 66. The reservoir 66 is also connected to another reservoir 68 which contains, for example, an aqueous solution in which the organic salt is at least partially soluble. The two reservoirs 66 and 68 are separated by a rigid, semi-permeable membrane 70, which is partially or completely impermeable to the salt in reservoir 66 and partially or fully permeable to the solution in reservoir 68. There is also an optional fill port or vent 72 in communication with the reservoir 68, through which material can be added to or removed from the reservoir 68. Using this microneedle device 60, water can be drawn from the reservoir 68 across the semi-permeable membrane 70 into the reservoir 66 due to osmosis caused by the presence of salt in the reservoir 66. The flow of water will cause the volume of reservoir 66 to increase and thereby force the volume of reservoir 62 to decrease, which causes material to expel from reservoir 62 through microneedles 14.

In an alternate form, delivery is initiated by opening the pathway between the reservoir and the microneedle tip, or unblocking the tip openings, and simply allowing the drug to be delivered by diffusion, that is, a passive process.

Figure 6A:
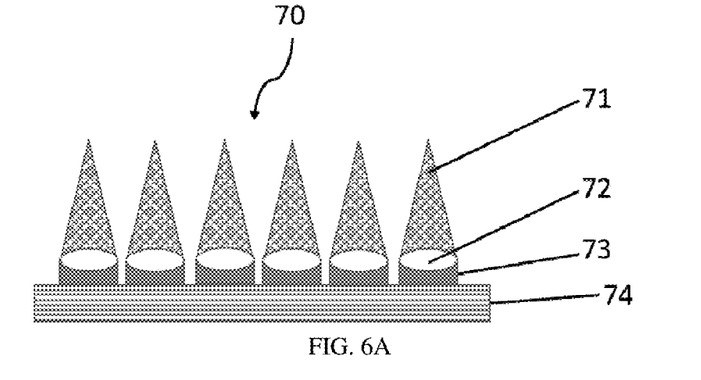
FIGS. 6A-6C are cross-sectional views of microneedle devices with microneedles containing a biodegradable and/or biodissolvable polymer and a drug (e.g., LT3, or LT3 and LT4, or a salt thereof) to be delivered to a patient.
Figure 6B:
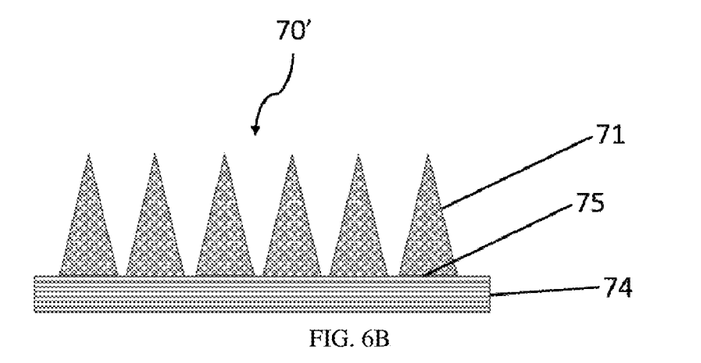
Figure 6C:
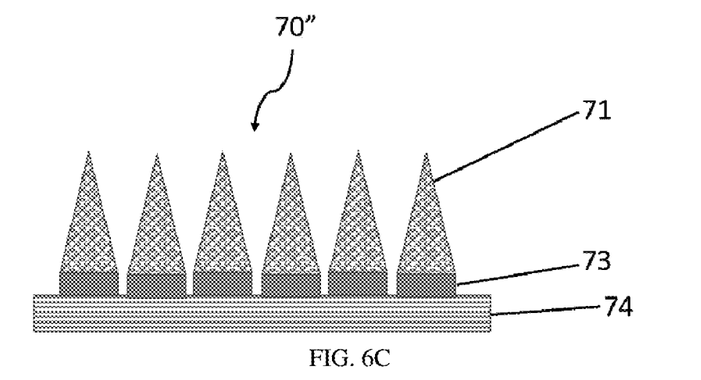

Other illustrative forms of the microneedle device are shown in FIGS. 6A-6C. Referring to FIG. 6A, the microneedle device 70 includes substrate 74 (that can be the same as the previously described substrate 12), from which a three-dimensional array of microneedles 71 protrude. The microneedle device 70 also includes pedestals 73 on the substrate, and bubbles 72 between the pedestals 73 and the microneedles 71. In FIG. 6B, the pedestals 73 and bubbles 72 are absent, such that joints 75 exist, which are formed at the interface of the substrate 74 and the microneedles 71. In FIG. 6C, the bubbles 72 are absent, and the microneedles are on pedestals 73 supported by the substrate 74. The pedestals can facilitate complete insertion of the microneedles into a skin or other surface. The pedestal can be of the same or different material as the substrate. In some forms, the pedestal is of the same material as the substrate. Although shown as straight, the pedestals in these devices can be tapered. In the tapered structure, the side in contact with the substrate can be wider than the side in contact with the microneedles.

Feedback about Delivery

In some forms, the microneedle device includes a feedback means so that the user can (1) determine whether delivery has been initiated; and/or (2) confirm that the reservoir has been emptied, that is delivery complete. Representative feedback means include a sound, a color (change) indicator, or a change in the shape of a deformable reservoir. In another form, the feedback for completion of delivery is simply that the reservoir is pressed flat against the back of the substrate and cannot be further deformed.

Feedback about Penetration of the Microneedles into the Tissue

The user of the microneedle device typically can determine if the microneedles have been properly inserted into the skin or other tissue through visual or tactile means, that is assessing whether the substrate has been pressed essentially flush to the tissue surface. For example, if a puddle of liquid drug composition appears near the microneedle device, then the user may infer that the microneedles are not fully inserted, suggesting that the microneedle device needs to be reapplied. The liquid drug compositions can include a coloring agent to enhance the visual feedback.

In a more complex form, an electrical or chemical measurement is adapted to provide the feedback. For example, penetration can be determined by measuring a change in electrical resistance at the skin or other tissue, or a pH change. Alternately, needle-to-needle electrical resistance can be measured. In some forms, the microneedle device includes a disposable cartridge containing the microneedles. In these microneedle devices, an LED (e.g., green light/red light) or liquid crystal display can be provided with the reusable portion of the microneedle device.

Controlling the Delivery Rate

The microneedle device must be capable of transporting drug across or into the tissue at a useful rate. For example, the microneedle device must be capable of delivering drug at a rate sufficient to be therapeutically useful. The rate of delivery of the drug composition can be controlled by altering one or more of several design variables. For example, the amount of material flowing through the needles can be controlled by manipulating the effective hydrodynamic conductivity (the volumetric through-capacity) of a single device array, for example, by using more or fewer microneedles, by increasing or decreasing the number or diameter of the bores in the microneedles, or by filling at least some of the microneedle bores with a diffusion-limiting material. It is preferred, however, to simplify the manufacturing process by limiting the needle design to two or three "sizes" of microneedle arrays to accommodate, for example small, medium, and large volumetric flows, for which the delivery rate is controlled by other means.

Other means for controlling the rate of delivery include varying the driving force applied to the drug composition in the reservoir. For example, in passive diffusion systems, the concentration of drug in the reservoir can be increased to increase the rate of mass transfer. In active systems, for example, the pressure applied to the reservoir can be varied, such as by varying the spring constant or number of springs or elastic bands.

In either active or passive systems, the barrier material can be selected to provide a particular rate of diffusion for the drug molecules being delivered through the barrier at the needle inlet.

Other forms of controlling the release of drug involves including the drug (e.g., LT3 or salt thereof) in microneedles containing biodegradable and/or biodissolvable compound (e.g., biodegradable and/or biodissolvable polymers). Upon degradation or hydrolysis of the materials, the drug is slowly released in the body over time, following attachment of the microneedle device to the skin of a patient. Suitable biodegradable and/or biodissolvable polymers include, but are not limited to polyvinyl pyrrolidone, polyvinyl alcohols, polysaccharides (e.g. hyaluronic acid, chitosan, cellulose, alginate); poly(esters) (e.g. poly(lactic acid), poly(glycolic acid), poly(lactide-co-glycolide), poly(caprolactones)); poly (orthoesters); polylysine; poly(ethylene imine); poly(acrylic acid); poly(urethanes); poly(anhydrides); poly(trimethylene carbonate); poly(ethyleneimine), poly(beta amino esters), and copolymers of these and/or other polymers.

The drug (e.g., LT3 or salt thereof) can also be provided in a controlled release formulation in at least one of the reservoirs that is not a microneedle. In these forms, the formulation in the reservoir can be a hydrogel containing the drug; or the formulation contains nanoparticles and/or microparticles containing the drug (e.g., LT3 or salt thereof). Materials that can be used to form suitable hydrogel include polymers such as polysaccharides (e.g. hyaluronic acid, chitosan, cellulose, alginate); poly(-hydroxyethyl methacrylate) (pHEMA); poly(ethylene glycol) (PEG); poly(vinyl alcohol) (PVA); PEG-polyester copolymers; poly(N-isopropylacrylamide) (pNIPAAm); poly(ethylene oxide)-poly(propylene oxide)-poly(ethylene oxide), and gelatin. Materials that can be used to form suitable nanoparticles and/or microparticles include: carbohydrates such as alginate, cellulose; polyhydroxyalkanoates; polyamides; polyphosphazenes; polypropylfumarates; polyethers; polyacetals; polycyanoacrylates; biodegradable polyurethanes; polycarbonates; polyanhydrides; poly(orthoesters), and other biodegradable polyesters.

Multi-Cartridge Microneedle Device

A modification of the disposable, single use microneedle device utilizes a reusable triggering device (e.g., a plunger) in combination with a cartridge containing one or more, preferably a plurality, of single-use microneedle devices. For example, the cartridge can be a circular disk having 10 or 12 microneedle arrays connected to a single-dose reservoir, wherein the cartridge can be loaded into and unloaded from the triggering device. The triggering device can, for example, be designed to move a new dose into position for delivery, compress the reservoir to deliver the drug, and then eject or immobilize the used array. This type of reusable triggering device also can include a power source, such as a battery, used to operate a built-in measurement device, for example, for analyte measurement of interstitial fluids or electrical verification of needle penetration into skin, as described earlier in this document.

Microneedle Device Packaging

In some forms following manufacture of the microneedle device, it is packaged for storage, shipment, and sale before use. The packaging should prevent contamination and damage. The packaging also should prevent premature triggering or release of any drug or vehicle contents from the reservoir.

It is particularly important that, the microneedle device is provided with a removable protective cover or cushion that protects the microneedles from damage. The protective cover also can function to keep the drug material from prematurely leaking out of the microneedles. In a preferred form, an adhesive material or gel film used to selectively secure the cover over the microneedles. In an alternate form, the film is antiseptic, and following removal can serve as a wipe to prepare the skin surface before insertion of the microneedles.

The packaging also can be adapted to serve as a vessel for safely disposing of the used microneedle device. In a preferred form, the single-use microneedles are provided a device or material to shear the needles from the substrate or plug the microneedles, so as to prevent undesirable reuse of the microneedle device. In one form, the inner back of the reservoir is provided with a tacky substance. When the reservoir is compressed against the back of the substrate following delivery of the reservoir contents, the tacky substance is driven into the opening of the microneedles, plugging them. In one form of this microneedle device, the tacky material dries and hardens so that the substance cannot readily be removed.

Those skilled in the art will recognize, or be able to ascertain using no more than routine experimentation, many equivalents to the specific forms of the invention described herein. Such equivalents are intended to be encompassed by the following claims.

I claim:

1. A microneedle device comprising
    a) a plurality of biodegradable microneedles each having a base end and a tip;
    b) a substrate to which the base end of the microneedle is secured or integrated; and
    c) an effective amount of liothyronine (LT3) or a salt thereof in a sustained controlled release formulation which releases transdermally to maintain therapeutically effective serum levels of free or total T3, in a patient with hypothyroidism.

2. The microneedle device of claim 1, wherein the microneedle device is configured to provide sustained controlled release of an amount of LT3 or salt thereof to maintain stable levels of serum free or total T3 in a patient with hypothyroidism.

3. The microneedle device of claim 1, wherein the microneedle device is configured to provide sustained controlled release of an amount of LT3 or salt thereof to maintain stable levels of serum free T3 or total T3 in a patient with hypothyroidism.

4. The microneedle device of claim 1, wherein the microneedle device comprises a reservoir configured to provide controlled, sustained release of LT3.

5. The microneedle device of claim 1, wherein the microneedles comprise LT3 or a salt thereof which is released from the microneedles after administration to a patient with hypothyroidism.

6. The microneedle device of claim 5, wherein the microneedles further comprise levothyroxine (LT4) or a salt thereof.

7. The microneedle device of claim 6, wherein the microneedles comprise LT3 and LT4 and the LT4 or salt thereof is either in the same microneedle with the LT3 or salt thereof, or a different microneedle from that with the LT3 or salt thereof.

8. The microneedle device of claim 1, wherein the microneedles comprise biodegradable polymers.

9. The microneedle device of claim 7, wherein the polymers are selected from the group consisting of polyvinyl pyrrolidone, polyvinyl alcohols, polysaccharides, poly(esters), poly(orthoesters), polylysine, poly(ethylene imine), poly(acrylic acid), poly(urethanes), poly(anhydrides), poly(trimethylene carbonate), poly(ethyleneimine), poly(beta amino esters), and copolymers thereof.

10. The microneedle device of claim 1, wherein the microneedle device further comprises LT4 which is released transdermally.

11. The microneedle device of claim 1, wherein the amount of LT3 is effective to treat an obese patient with hypothyroidism.

12. The microneedle device of claim 1, further comprising a chemical permeation enhancer (CPE).

13. The microneedle device of claim 12, wherein the CPE is anionic, cationic, zwitterionic, or nonionic.

14. The microneedle device of claim 1, further comprising therapeutic agent other than LT3, a prophylactic agent, or a diagnostic agent.

15. The microneedle device of claim 14, wherein the therapeutic, prophylactic or diagnostic agent is selected from the group consisting of peptides, proteins, carbohydrates, nucleic acids, lipids, organic molecules, biologically active inorganic molecules, and combinations thereof.

16. The microneedle device of claim 14, wherein the diagnostic agent is selected from the group consisting of radioactive isotopes, radioopaque agents, chromatographic labels, fluorescent labels, and enzymatic labels.

17. The microneedle device of claim 1, comprising a therapeutic agent selected from the group consisting of LT4 or LT3 N-methyl, LT4 or LT3 N-ethyl, LT4 or LT3 N-triphenyl, LT4 or LT3 N-propyl, LT4 or LT3 N-isopropyl, LT4 or LT3 N-tertiary butyl, 3,5-dimethyl-4-(4'-hydroxy-3'-isopropylbenzyl)-phenoxy acetic acid (GC-I), 3,5-diiodothyropropionic acid (DITPA), tetraiodothyroacetic acid (TETRAC), and triiodothyroacetic acid (TRIAC), or their salts.

18. The microneedle device of claim 1, wherein the microneedles have a length between 10 μm and 1 mm, inclusive.

19. The microneedle device of claim 1, wherein the microneedles provide an insertion depth between about 100 µm and 700 µm.

20. The microneedle device of claim 1, further comprising an adhesive for securing the microneedle device during delivery.

21. The microneedle device of claim 1, wherein the substrate is flexible.

22. A method for delivering LT3 or salt thereof transdermally to a patient with hypothyroidism, comprising:
providing the microneedle device of claim 1.

23. The method of claim 22, further comprising placing the microneedle device on the skin of a patient with hypothyroidism.

24. The method of claim 22, wherein the patient is a human or a veterinary patient.

25. The microneedle device of claim 1 wherein the microneedle device is configured to produce an improved serum free T3:free T4 ratio in a patient with hypothyroidism.

26. The microneedle device of claim 1 wherein the microneedle device is configured to produce improved serum levels of thyroid stimulating hormone (TSH) in a patient with hypothyroidism.

* * * * *